(12) United States Patent
Belanger et al.

(10) Patent No.: US 6,287,834 B1
(45) Date of Patent: Sep. 11, 2001

(54) CHARACTERIZATION AND USE OF AN ISOLATED URIDINE DIPHOSPHO-GLUCURONOSYLTRANSFERASE

(75) Inventors: Alain Belanger; Dean W. Hum; Martin Beaulieu; Eric Levesque, all of Quebec (CA)

(73) Assignee: Endorecherche, Inc. (CA)

( * ) Notice: Subject to any disclaimer, the term of this patent is extended or adjusted under 35 U.S.C. 154(b) by 0 days.

(21) Appl. No.: 09/180,852

(22) PCT Filed: May 16, 1997

(86) PCT No.: PCT/CA97/00328

§ 371 Date: Feb. 8, 1999

§ 102(e) Date: Feb. 8, 1999

(87) PCT Pub. No.: WO97/44466

PCT Pub. Date: Nov. 27, 1997

Related U.S. Application Data

(63) Continuation-in-part of application No. 08/649,319, filed on May 17, 1996, now abandoned.

(51) Int. Cl.[7] .............................. C12P 21/06; C12N 9/00; C12N 9/10; C12N 1/20; C12N 15/00
(52) U.S. Cl. ................. 435/193; 435/69.1; 435/183; 435/252.3; 435/254.11; 435/320.1; 536/23.2
(58) Field of Search .................. 435/193, 252.3, 435/254.11, 325, 320.1; 536/23.1, 23.2

(56) References Cited

FOREIGN PATENT DOCUMENTS 9503788   2/1995  (EP).

OTHER PUBLICATIONS

Beaulieu, et al., *Clinical and Investigative Medicine*, 18(4):B41 (1995).
Beaulieu, et al., *Journal of Biological Chemistry*, 271(37):22855–22862 (1996).
Belanger, et al., *Molecular and Cellular Endocrinology*, 113:165–173 (1995).
Belanger, et al., *J. Steroid Biochem. and Molecular Biology*, 40(4–6):593–598 (1991).
Guillemette, et al., *J. Steroid Biochem. and Molecular Biology*, 57(3–4):225–231 (1996).
Guillemette, et al., *Molecular and Cellular Endocrinology*, 107(2):131–139 (1994).
Towbin, et al., *Proc. Nat'l. Acad. Sci.*, 76:4350–54 (1979).
Burnette, et al., *Biochem.*, 112:195–203 (1981).
Hélene, et al., *Biochimica et Biophysica Acta*, 1049:99–125 (1990).
Guillemette, et al., *Endocrinology*, 137(7):1–8 (1996).
Green, et al., *Drug Metabolism and Disposition*, 22(5):799–805 (1994).
Chen, et al., *Biochemistry*, 32:10648–10657 (1993).
Fournel–Gigleux, et al., *Molecular Pharmacology*, 39(2):177–183 (1991).
Coffman, et al., *Archives of Biochemistry and Biophysics*, 281(1):170–175 (1990).
Ngo, et al., Computational Complexity, Protein Structure Prediction, and the Lveinthal Paradox, In The Protein Folding Problem and Tertiary Structure Prediction, Eds. Merz et al., Birkhauser, Boston, MA., pp. 491–495 (1994).
International Preliminary examination Report on Corresponding PCT Patent Application No. PCT/CA97/00328 (Sep. 1998).

*Primary Examiner*—Ponnathapu Achutamurthy
*Assistant Examiner*—Manjunath N. Rao

(57) ABSTRACT

A uridine diphospho-glucuronosyltransferase (UGTB217) is provided. Methods of producing the enzyme and using the enzyme to identify potential compounds which inhibit or alter the activity of the enzyme are described. In addition, methods of using antibodies to localize the protein, or using the gene sequence or portions thereof for probes or using the gene sequence to produce expression-disrupting sense or antisense DNA fragments thereof, or antisense RNA, are provided.

11 Claims, 5 Drawing Sheets

CHARACTERIZATION AND USE OF AN ISOLATED URIDINE DIPHOSPHO-GLUCURONOSYLTRANSFERASE

This Application is a Continuation-in-Part of Ser. No. 08/649,319 filed May 17, 1996 now ABN; and also a 371 of PCT/CA97/00328 filed May 16, 1997.

BACKGROUND OF THE INVENTION

1. Field of the Invention

The present invention relates to the isolation, characterization and use of a novel enzyme which belongs to a family of enzymes which catalyze the transfer of glucuronic acid from uridine diphospho-glucuronic acid to a wide variety of lipid soluble drugs, environmental chemicals and endogenous substances, and more particularly, to the characterization of, and isolation of the cDNA which encodes, a novel uridine diphospho-glucuronosyltransferase (UGT) (hereinafter UGT2B17) which has been found to conjugate androgenic compounds, particularly $C_{19}$ steroids. The use of this enzyme in an assay is also described, as are several other uses of the DNA, fragments thereof, antisense fragments thereof and antibodies thereto.

2. Description of the Related Art

The enzymes identified as UGTs are a family of enzymes which catalyze the glucuronidation process in which glucuronic acid is transferred from uridine diphospho-glucuronic acid to a wide variety of lipid soluble drugs, environmental chemicals and endogenous substances such as bilirubin, steroid hormones and thyroxine. Generally, glucuronidation occurs in the liver and kidney and is responsible for the elimination of glucuronide derivatives from the body. However, UGT activity has also been identified in numerous tissues, including prostate, testis, skin, breast, brain and ovary tissues, and in breast and prostate tumor cell lines.

The UGT family of enzymes has been classified into two subfamilies, UGT1 and UGT2. The UGT1 family are generally known to be involved in the glucuronidation of planar and bulky phenol substrates and bilirubin, however, some members of the UGT1 family can conjugate estrogens. Enzymes of the UGT2 family are divided into two subfamilies, UGT2A which includes enzymes encoded by genes expressed in the olfactory epithelium and UGT2B which includes enzymes that catalyze the glucuronidation of bile acids, $C_{19}$ steroids, $C_{18}$ steroids, fatty acids, carboxylic acids, phenols and carcinogens, such as benzopyrene and 2-acetylaminofluorene. Several members of the UGT2B family have been isolated from human liver and been characterized. It has been found that there is an overlap in the substrate specificity among the UGT2B enzymes.

The present invention relates to a novel UGT which is a member of the UGT2B family and which is described in detail below.

SUMMARY OF THE INVENTION

It is an object of the present invention to provide a novel uridine diphospho-glucuronosyltransferase (UGT) which is identified as UGT2B17.

It is also an object of the present invention to provide a UGT which has been shown to conjugate $C_{19}$ steroids at the 3α-hydroxy and 17β-hydroxy groups.

It is an additional object of his invention to provide a UGT which is involved in the conversion of androsterone to androsterone-glucuronic acid.

It is also an object of the present invention to provide a UGT which has specificity for androgenic compounds, particularly $C_{19}$ steroids compounds including androsterone (ADT), testosterone, dihydrotestosterone (DHT), and androstane-3α, 17β-diol (3α-DIOL), and for eugenol, 4-methylumbelliferone.

It is a further object of this invention to provide nucleotide sequences for UGT2B17.

It is also an object of this invention to provide methods of using UGT2B17 in an assay to identify compounds which inhibit the activity of this enzyme or using antibodies to UGT2B17 for detecting and quantifying the enzyme.

These and other objects are discussed herein.

In particular, a novel uridine diphospho-glucuronosyltransferase, UGT2B17, has been identified and characterized. The primary protein structure UGT2B17 was found to include 530 amino acids (SEQ ID No. 2) and to have an apparent molecular weight of 53 kilodaltons (when measured by SDS-PAGE). The protein is encoded by nucleotides +52 through 1644, including the stop codon (amino acids 1 through 530), numbered in the 5' to 3' direction, in the following sequence (SEQ ID Nos. 1 and 2):

```
GGCACGAGGA AAGAAACAAC AACTGGAAAA GAAGCATTGC ATAAGACCAG G ATG TCT          57
                                                         Met Ser
                                                          1

CTG AAA TGG ATG TCA GTC TTT CTG CTG ATG CAG CTC AGT TGT TAC TTT   105
            Leu Lys Trp Met Ser Val Phe Leu Leu Met Gln Leu Ser Cys Tyr Phe
                    5               10                  15

AGC TCT GGG AGT TGT GGA AAG GTG CTG GTG TGG CCC ACA GAA TAC AGC   153
            Ser Ser Gly Ser Cys Gly Lys Val Leu Val Trp Pro Thr Glu Tyr Ser
                    20              25                  30

CAT TGG ATA AAT ATG AAG ACA ATC CTG GAA GAG CTT GTT CAG AGG GGT   201
            His Trp Ile Asn Met Lys Thr Ile Leu Glu Glu Leu Val Gln Arg Gly
            35                  40                  45                  50

CAT GAG GTG ATT GTG TTG ACA TCT TCG GCT TCT ATT CTT GTC AAT GCC   249
            His Glu Val Ile Val Leu Thr Ser Ser Ala Ser Ile Leu Val Asn Ala
                                55                  60                  65

AGT AAA TCA TCT GCT ATT AAA TTA GAA GTT TAT CCT ACA TCT TTA ACT   297
            Ser Lys Ser Ser Ala Ile Lys Leu Glu Val Tyr Pro Thr Ser Leu Thr
                            70                  75                  80
```

-continued

```
AAA AAT GAT TTG GAA GAT TTT TTT ATG AAA ATG TTC GAT AGA TGG ACA      345
Lys Asn Asp Leu Glu Asp Phe Phe Met Lys Met Phe Asp Arg Trp Thr
         85                  90                  95

TAT AGT ATT TCA AAA AAT ACA TTT TGG TCA TAT TTT TCA CAA CTA CAA      393
Tyr Ser Ile Ser Lys Asn Thr Phe Trp Ser Tyr Phe Ser Gln Leu Gln
        100                 105                 110

GAA TTG TGT TGG GAA TAT TCT GAC TAT AAT ATA AAG CTC TGT GAA GAT      441
Glu Leu Cys Trp Glu Tyr Ser Asp Tyr Asn Ile Lys Leu Cys Glu Asp
115                 120                 125                 130

GCA GTT TTG AAC AAG AAA CTT ATG AGA AAA CTA CAA GAG TCA AAA TTT      489
Ala Val Leu Asn Lys Lys Leu Met Arg Lys Leu Gln Glu Ser Lys Phe
            135                 140                 145

GAT GTC CTT CTG GCA GAT GCC GTT AAT CCC TGT GGT GAG CTG CTG GCT      537
Asp Val Leu Leu Ala Asp Ala Val Asn Pro Cys Gly Glu Leu Leu Ala
        150                 155                 160

GAA CTA CTT AAC ATA CCC TTT CTG TAC AGT CTC CGC TTC TCT GTT GGC      585
Glu Leu Leu Asn Ile Pro Phe Leu Tyr Ser Leu Arg Phe Ser Val Gly
        165                 170                 175

TAC ACA GTT GAG AAG AAT GGT GGA GGA TTT CTG TTC CCT CCT TCC TAT      633
Tyr Thr Val Glu Lys Asn Gly Gly Gly Phe Leu Phe Pro Pro Ser Tyr
180                 185                 190

GTA CCT GTT GTT ATG TCA GAA TTA AGT GAT CAA ATG ATT TTC ATG GAG      681
Val Pro Val Val Met Ser Glu Leu Ser Asp Gln Met Ile Phe Met Glu
195                 200                 205                 210

AGG ATA AAA AAT ATG ATA TAT ATG CTT TAT TTT GAC TTT TGG TTT CAA      729
Arg Ile Lys Asn Met Ile Tyr Met Leu Tyr Phe Asp Phe Trp Phe Gln
            215                 220                 225

GCA TAT GAT CTG AAG AAG TGG GAC CAG TTT TAT AGT GAA GTT CTA GGA      777
Ala Tyr Asp Leu Lys Lys Trp Asp Gln Phe Tyr Ser Glu Val Leu Gly
            230                 235                 240

AGA CCC ACT ACA TTA TTT GAG ACA ATG GGG AAA GCT GAA ATG TGG CTC      825
Arg Pro Thr Thr Leu Phe Glu Thr Met Gly Lys Ala Glu Met Trp Leu
        245                 250                 255

ATT CGA ACC TAT TGG GAT TTT GAA TTT CCT CGC CCA TTC TTA CCA AAT      873
Ile Arg Thr Tyr Trp Asp Phe Glu Phe Pro Arg Pro Phe Leu Pro Asn
        260                 265                 270

GTT GAT TTT GTT GGA GGA CTT CAC TGT AAA CCA GCC AAA CCC TTG CCT      921
Val Asp Phe Val Gly Gly Leu His Cys Lys Pro Ala Lys Pro Leu Pro
275                 280                 285                 290

AAG GAA ATG GAA GAG TTT GTG CAG AGC TCT GGA GAA AAT GGT ATT GTG      969
Lys Glu Met Glu Glu Phe Val Gln Ser Ser Gly Glu Asn Gly Ile Val
                295                 300                 305

GTG TTT TCT CTG GGG TCG ATG ATC AGT AAC ATG TCA GAA GAA AGT GCC     1017
Val Phe Ser Leu Gly Ser Met Ile Ser Asn Met Ser Glu Glu Ser Ala
            310                 315                 320

AAC ATG ATT GCA TCA GCC CTT GCC CAG ATC CCA CAA AAG GTT CTA TGG     1065
Asn Met Ile Ala Ser Ala Leu Ala Gln Ile Pro Gln Lys Val Leu Trp
        325                 330                 335

AGA TTT GAT GGC AAG AAG CCA AAT ACT TTA GGT TCC AAT ACT CGA CTG     1113
Arg Phe Asp Gly Lys Lys Pro Asn Thr Leu Gly Ser Asn Thr Arg Leu
        340                 345                 350

TAT AAG TGG TTA CCC CAG AAT GAC CTT CTT GGT CAT CCC AAA ACC AAA     1161
Tyr Lys Trp Leu Pro Gln Asn Asp Leu Leu Gly His Pro Lys Thr Lys
355                 360                 365                 370

GCT TTT ATA ACT CAT GGT GGA ACC AAT GGC ATC TAT GAG GCG ATC TAC     1209
Ala Phe Ile Thr His Gly Gly Thr Asn Gly Ile Tyr Glu Ala Ile Tyr
                375                 380                 385

CAT GGG ATC CCT ATG GTG GGC ATT CCC TTG TTT GCG GAT CAA CAT GAT     1257
His Gly Ile Pro Met Val Gly Ile Pro Leu Phe Ala Asp Gln His Asp
            390                 395                 400
```

-continued

```
AAC ATT GCT CAC ATG AAA GCC AAG GGA GCA GCC CTC AGT GTG GAC ATC      1305
Asn Ile Ala His Met Lys Ala Lys Gly Ala Ala Leu Ser Val Asp Ile
        405                 410                 415

AGG ACC ATG TCA AGT AGA GAT TTG CTC AAT GCA TTG AAG TCA GTC ATT      1353
Arg Thr Met Ser Ser Arg Asp Leu Leu Asn Ala Leu Lys Ser Val Ile
        420                 425                 430

AAT GAC CCT ATC TAT AAA GAG AAT ATC ATG AAA TTA TCA AGA ATT CAT      1401
Asn Asp Pro Ile Tyr Lys Glu Asn Ile Met Lys Leu Ser Arg Ile His
435                 440                 445                 450

CAT GAT CAA CCG GTG AAG CCC CTG GAT CGA GCA GTC TTC TGG ATT GAG      1449
His Asp Gln Pro Val Lys Pro Leu Asp Arg Ala Val Phe Trp Ile Glu
            455                 460                 465

TTT GTC ATG CGC CAT AAA GGA GCC AAG CAC CTT CGG GTC GCA GCC CAC      1497
Phe Val Met Arg His Lys Gly Ala Lys His Leu Arg Val Ala Ala His
            470                 475                 480

AAC CTC ACC TGG ATC CAG TAC CAC TCT TTG GAT GTG ATA GCA TTC CTG      1545
Asn Leu Thr Trp Ile Gln Tyr His Ser Leu Asp Val Ile Ala Phe Leu
            485                 490                 495

CTG GCC TGC GTG GCA ACT ATG ATA TTT ATG ATC ACA AAA TGT TGC CTG      1593
Leu Ala Cys Val Ala Thr Met Ile Phe Met Ile Thr Lys Cys Cys Leu
        500                 505                 510

TTT TGT TTC CGA AAG CTT GCC AAA ACA GGA AAG AAG AAG AAA AGG GAT      1641
Phe Cys Phe Arg Lys Leu Ala Lys Thr Gly Lys Lys Lys Lys Arg Asp
515                 520                 525                 530

TAG TTATATCAAA AGCCTGAAGT GGAATGACCA AAAGATGGGA CTCCTCCTTT           1694
 *

ATTCCAGCAT GGAGGGTTTT AAATGGAGGA TTTCCTTTTT CCTGCGACAA AACGTCTTTT    1754

CACAACTTAC CCTGTTAAGT CAAAATTTAT TTTCCAGGAA TTTAATATGT ACTTTAGTTG    1814

GAATTATTCT ATGTCAATGA TTTTTAAGCT ATGAAAAATA ATAATATAAA ACCTTATGGG    1874

CTTATATTGA AATTTATTAT TCTAATCCAA AAGTTACCCC ACACAAAAGT TACTGAGCTT    1934

CCTTATGTTT CACACATTGT ATTTGAACAC AAAACATTAA CAACTCCACT CATAGTATCA    1994

ACATTGTTTT GCAAATACTC AGAATATTTT GGCTTCATTT TGAGCAGAAT TTTTGTTTTT    2054

AATTTTGCCA ATGAAATCTT CAATAATTAA AAAAAAAAAA AAAAAAAAA AAA           2107
```

The open reading frame of 1590 bases is flanked by a 5'-untranslated region of 51 base pairs and a 3'-untranslated region of 463 base pairs. A more detailed description of the sequences will be provided infra.

The present invention includes methods for the synthetic production of UGT2B17, as well as peptides that are biologically functionally equivalent antibodies to UGT2B17, and uses of the antibodies to detect and quantify the enzyme.

The nucleotide sequence which encodes UGT2B17 and recombinant expression vectors which include the sequence may be modified so long as they continue to encode a functionally equivalent enzyme. Moreover, it is contemplated, within the invention, that codons within the coding region may be altered inter alia, in a manner which, given the degeneracy of the genetic code, continues to encode the same protein. It is believed that nucleotide sequences analogous to SEQ ID No. 1, or those that hybridize under stringent conditions to the coding region of SEQ ID No. 6 (or its complement), are likely to encode a UGT2B17 functionally equivalent to that encoded by the coding region of SEQ ID No. 1, especially if such analogous nucleotide sequence is at least 1500 nucleotides, and most preferably at least 1590 nucleotides in length. As used herein, except where otherwise specified, "stringent conditions" means 0.1x SSC (0.3 M sodium chloride and 0.03M sodium citrate) and 0.1% sodium dodecyl sulphate (SDS) and 60° C.

It is also likely that tissues or cells from human or non-human sources, particularly tissues or cells which include steroids, include a UGT2B17 sufficiently analogous to human UGT2B17 to be used in accordance with the present invention. In particular, cDNA libraries prepared from cells, as described above, may be screened with probes in accordance with well known techniques prepared by reference to the nucleotides disclosed herein, and under varying degrees of stringency, in order to identify analogous cDNAs in other species. These analogous cDNAs are preferably at least 92% homologous to SEQ ID No. 1, and most preferably at least 95% homologous. They preferably include stretches of perfect identity at least 10 nucleotides long, more preferably stretches of 15, 20 or even 30 nucleotides of perfect identity. Appropriate probes may be prepared from SEQ ID No. 1 or fragments thereof of suitable length. preferably at least 15 nucleotides in length. Confirmation with at least two distinct probes is preferred. Alternative isolation strategies, such as polymerase chain reaction (PCR) amplification, may also be used.

Homologous UGT2B17s so obtained, as well as the genes encoding them, can be used in accordance with the invention in all of the ways for using SEQ ID No. 2 and SEQ ID No. 1, respectively.

Recombinant expression vectors can include the entire coding region for UGT2B17 as shown in SEQ ID No. 1, the coding region for UGT2B17 which has been modified as discussed herein, portions of the coding region for human UGT2B17 or analogous coding regions from other animals as described above, an antisense construct to UGT2B17, or portions of antisense constructs to UGT2B17.

In the context of the invention, "isolated" means having a higher purity than exists in nature, but does not require purification from a natural source. Isolated nucleotides encoding UGT2B17 may be produced synthetically, or by isolating cDNA obtained from a cDNA library prepared from mRNA encoding UGT2B17, or by any other method known in the art.

In one embodiment, the invention provides an isolated nucleotide sequence encoding uridine diphospho-glucuronosyltransferase 2B17, said sequence being sufficiently homologous to SEQ ID No. 1 or a complement thereof, to hybridize under stringent conditions to the coding region of SEQ ID No. 1 or a complement thereof and said sequence encoding an enzyme which catalyzes the conversion of androsterone to androsterone-glucuronic acid.

In a further embodiment, the invention provides an isolated nucleotide sequence comprising at least thirty consecutive nucleotides identical to thirty consecutive nucleotides in the coding region of SEQ ID No. 1, or the complement thereof.

In an additional embodiment, the invention provides a nucleotide sequence comprising nucleotides 52 to 927 of SEQ ID No. 1.

In another embodiment, the invention provides a nucleotide sequence comprising nucleotides 204 to 723 of SEQ ID No. 1.

In a further embodiment, the invention provides an isolated nucleotide sequence comprising SEQ ID No. 1.

In a further embodiment, a protein encoded by SEQ ID No. 1 is provided.

In another embodiment, isolated nucleic acid which encodes SEQ ID No. 2 is provided.

In a further embodiment, an isolated uridine diphospho-glucoronosyltransferase 2B17 enzyme having the same amino acid sequence as the amino acid sequence shown in SEQ ID NO. 2 is provided.

In another embodiment, the invention provides a recombinant expression vector comprising a promoter sequence operably linked to a coding sequence encoding uridine diphospho-glucuronosyltransferase 2B17, said coding sequence being sufficiently homologous to SEQ ID No. 1 or a complement thereof, to hybridize under stringent conditions to the coding region of SEQ ID No. 1 or a complement thereof and said coding sequence encoding an enzyme which catalyzes the conversion of androsterone to androsterone-glucuronic acid. SEQ ID NO. 1 and other DNA sequences encoding SEQ ID NO. 2 may be used as the coding region of a vector in accordance with the invention.

In a further embodiment, the invention provides host cells transformed or transfected with such vectors, and a method for producing uridine diphospho-glucuronosyltransferase 2B17 comprising the steps of preparing a recombinant host transformed or transfected with the vector of claim 3 and culturing said host under conditions which are conducive to the production of uridine diphospho-glucuronosyltransferase 2B17 by said host.

In an additional embodiment, the invention provides a kit for detecting antibodies to uridine diphospho-glucuronosyltransferase 2B17 comprising an immobilized antigenic composition comprising uridine diphospho-glucuronosyltransferase 2B17 or an antigenic fragment thereof and means for detecting a complex of said immobilized antigen and an antibody to said antigen.

In a further embodiment, a kit for detecting uridine diphospho-glucuronosyltransferase 2B17 comprising an immobilized antibody composition comprising antibodies to uridine diphospho-glucuronosyltransferase 2B17 or an antigenic fragment thereof and means for detecting a complex of said immobilized antibodies and uridine diphospho-glucuronosyltransferase 2B17 is provided.

In another embodiment, the invention provides antisera to purified or recombinant diphospho-glucuronosyltransferase 2B17.

In an additional embodiment, the invention provides a method of altering the concentration of an androgenic compound in a tissue comprising the step of administering uridine diphospho-glucuronosyltransferase 2B17.

In a further embodiment, the invention provides a method for detecting a localized concentration of uridine diphospho-glucuronosyltransferase 2B17 comprising administering labelled antibodies to said uridine diphospho-glucuronosyltransferase 2B17 and thereafter detecting said label.

In another embodiment, the invention provides a method of blocking the synthesis of uridine diphospho-glucuronosyltransferase 2B17, comprising the step of introducing a nucleotide sequence of at least 30 consecutive nucleotides in the coding region of SEQ ID No. 1, or the complement thereof.

In a further embodiment, a method of altering androgenic activity in a tissue comprising the step of administering uridine diphospho-glucuronosyltransferase 2B17 is provided.

In an additional embodiment, the invention provides a method for detecting an alteration in the level of androgenic activity in a sample comprising the step of determining a concentration of uridine diphospho-glucuronosyltransferase 2B17.

In another embodiment, the invention provides a method of detecting uridine diphospho-glucuronosyltransferase 2B17 in a test sample comprising contacting said test sample with antibodies to uridine diphospho-glucuronosyltransferase 2B17 and measuring formation of an immunocomplex between said antibodies and said uridine diphospho-glucuronosyltransferase 2B17.

In another embodiment, the invention provides a method of detecting antibodies to uridine diphospho-glucuronosyltransferase 2B17 in a test sample comprising contacting said test sample with uridine diphospho-glucuronosyltransferase 2B17 and measuring formation of an immunocomplex between said antibodies and said uridine diphospho-glucuronosyltransferase 2B17.

Other features and advantages of the present invention will become apparent from the following description of the invention which refers to the accompanying drawings.

BRIEF DESCRIPTION OF THE DRAWINGS

to FIGS. 4A and 4B are Lineweaver-Burk plots of ADT and DHT, and 3α-DIOL and testosterone (TESTO), respectively.

DETAILED DESCRIPTION OF THE INVENTION

Figure 1:
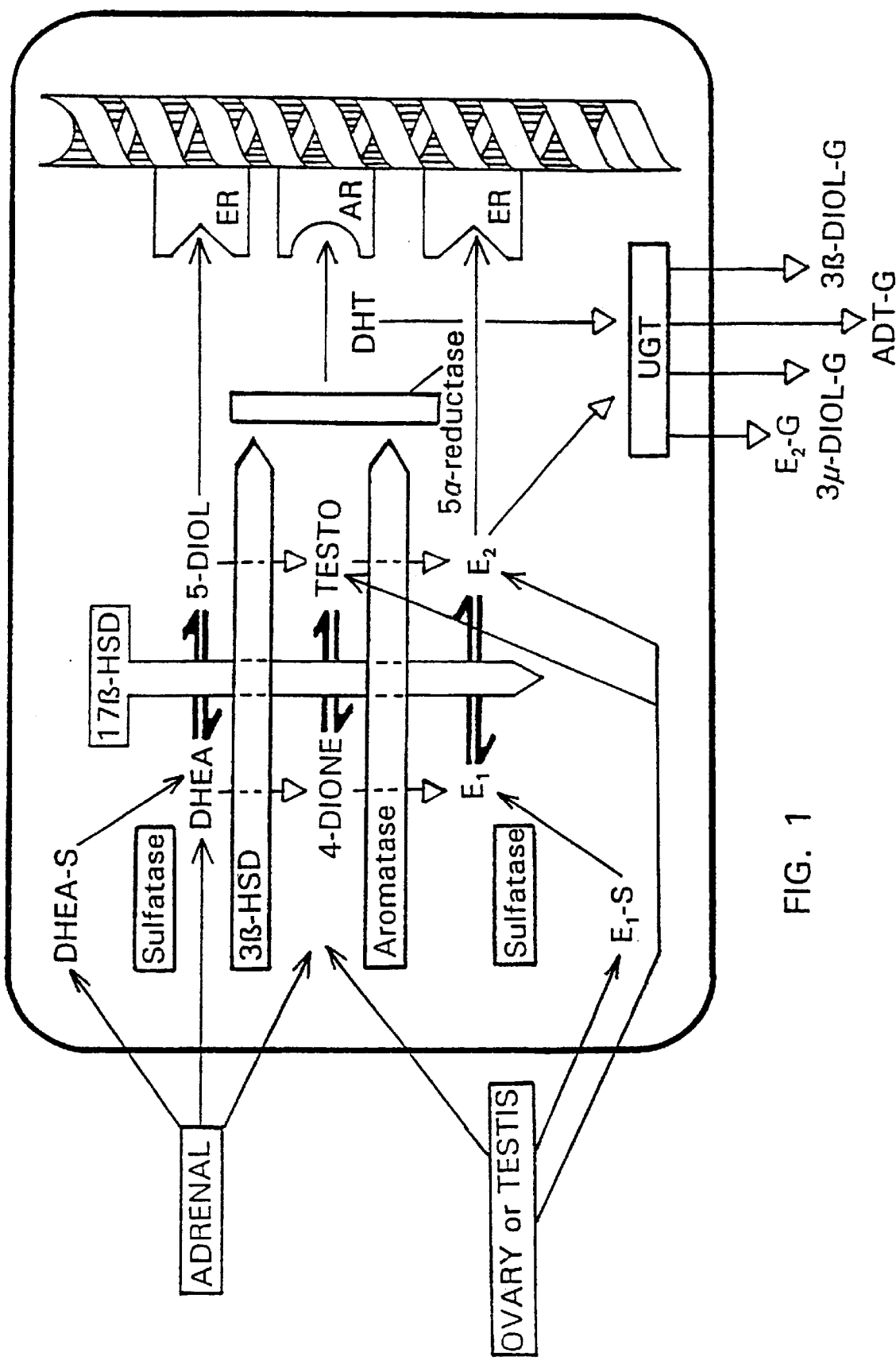
FIG. 1 is a general diagram of the steroidogenesis scheme which illustrates the role of uridine glucuronosyltransferases.

Glucuronidation is an irreversible enzymatic reaction in the pathway of steroid metabolism which is catalyzed by a uridine diphospho-glucuronosyltransferase (UGT). The UGTs catalyze the conjugation of the sugar acid moiety of uridine diphospho-glucuronic acid to steroids. It is shown that the formation of steroid glucuronides (-G) completely inactivates the androgens. Therefore, UGT enzymes can be used to regulate the concentration of substrates in tissues.

A cDNA encoding the enzyme, UGT2B17, has been isolated and encodes a protein having 530 amino acids with a measured molecular weight of 53 kilodaltons. The coding portion includes nucleotides +52 through 1644, including the stop codon (and encodes amino acids +1 through 530), numbered in the 5' to 3' direction. The protein structure contains a hydrophobic signal peptide at amino acids 5 through 12 which is responsible for directing the protein into the endoplasmic reticulum. In addition, the leader sequence contains a positively charged lysine at position 4 and terminates with a possible cleavage site at the cysteine residue at position 23. Further, UGT2B17 has a hydrophobic transmembrane region between amino acids 494 and 510 followed by a positively charged lysine residue. The UGT2B17 also includes three potential asparagine-linked glycosylation sites (NXS/T) at amino acid residues 65, 316, and 483.

A general diagram of steroidogenesis and the role of UGTs is provided is FIG. 1. In this figure, ER is an estrogen receptor; AR is an androgen receptor; E1 is estrone; E2 is estradiol; HSD is hydroxysteroid dehydrogenase; and DHEA is dehydroepiandrosterone.

It has been shown that the carboxy terminal region of the enzyme, which includes amino acids 290 through 530, contains a domain which is critical for the binding of uridine diphospho-glucuronic acid (UDPGA). Further, it has been shown that a domain for substrate specificity is present in the amino terminal region, particularly between amino acid residues 54 and 227.

The UGT2B17 enzyme can be produced by incorporating the nucleotide sequence for the coding portion of the gene into a vector which is then transformed or transfected into a host system which is capable of expressing the enzyme. The DNA can be maintained transiently in the host or can be stably integrated into the genome of the host cell.

In particular, for the cloning and expression of UGT2B17, any common expression vectors, such as plasmids, can be used. These vectors can be prokaryotic expression vectors including those derived from bacteriophage λ such as λgt11 and λEMBL3, *E. coli* strains such as pBR322 and Bluescript (Stratagene); or eukaryotic vectors, such as those in the pCMV family. A vector incorporating an isolated human cDNA (nucleotides 36 to 1870 of Sequence ID No. 1, ATCC Deposit No. 98228) for UGT2B17 was placed on deposit at the American Type Culture Collection (ATCC, Rockville, Md.), in accordance with the terms of the Budapest Treaty, and will be made available to the public upon issuance of a patent based on the present patent application. The gene may also be obtained by screening human prostate and LNCaP (a human prostatic adenocarcinoma cell line) cell cDNA libraries with probes derived from all or part of SEQ ID No. 1.

Figure 2:
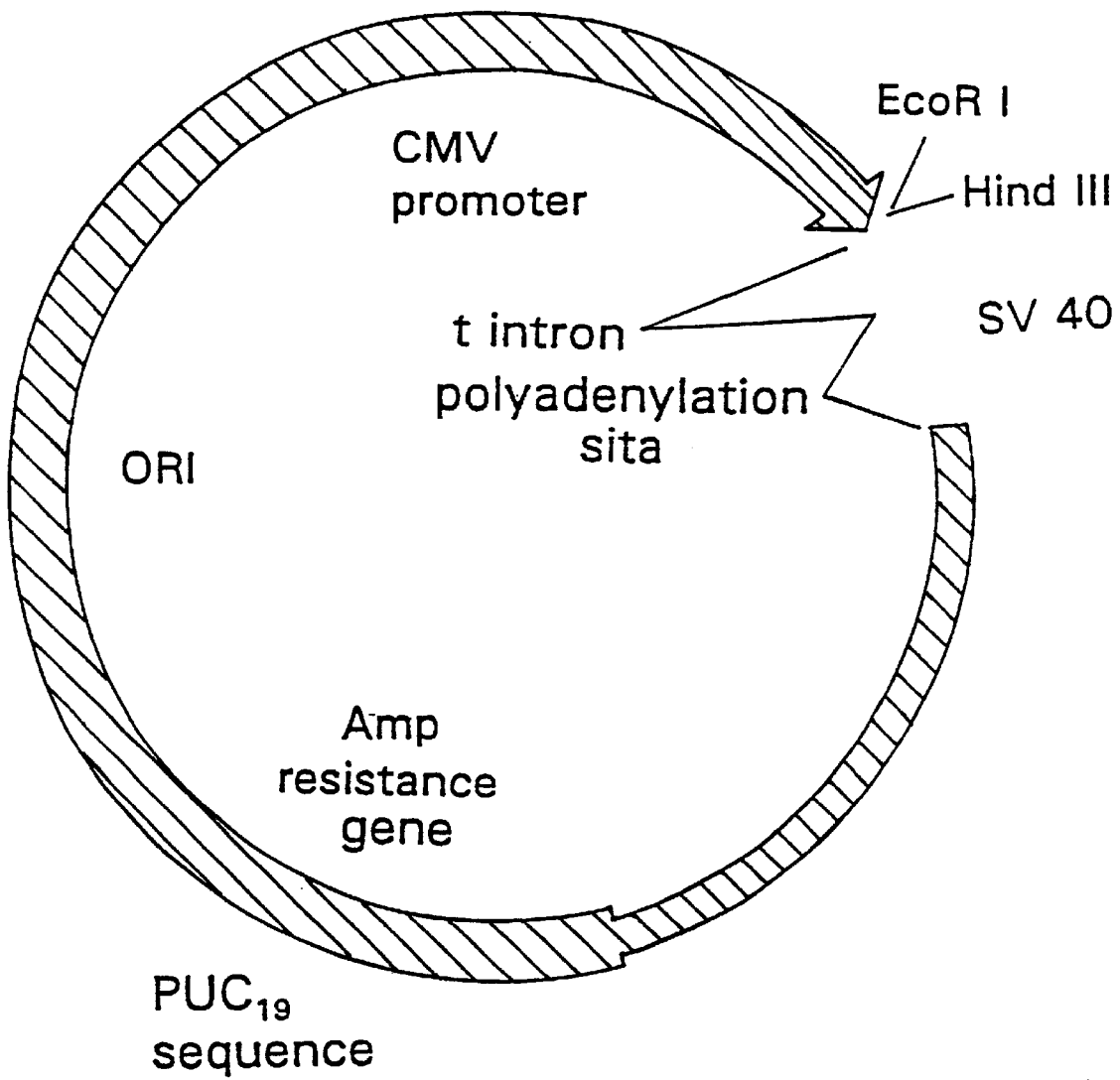
FIG. 2 is a map of a pCMV vector which is exemplary of one that can be used to transfect host cells in accordance with the invention.

Vectors which can be used in the practice of the invention generally include appropriate replication and control sequences which are compatible with the host system into which the vectors are transfected. A promoter sequence is generally included. For prokaryotes, some representative promoters include β-lactamase, lactose, and tryptophan. In mammalian cells, commonly used promoters include, but are not limited to, adenovirus, cytomegalovirus (CMV) and simian virus 40 (SV40). The vector can also optionally include, as appropriate, an origin of replication, ribosome binding sites, RNA splice sites, polyadenylation sites, transcriptional termination sequences and/or a selectable marker. It is well understood that there are a variety of vector systems with various characteristics which can be used in the practice of the invention. A map of the pCMV vector, which is an example of a vector which can be used in the practice of the invention, is provided in FIG. 2.

Commonly known host systems which are known for expressing an enzyme, and which may be transfected with an appropriate vector which includes the gene for UGT2B17 can be used in the practice of the invention. These host systems include prokaryotic hosts, such as *E. coli*, bacilli, such as *Bacillus subtilus*, and other enterobacteria, such as Salmonella, Serratia, and Pseudomonas species. Eukaryotic microbes, including yeast cultures, can also be used. The most common of these is *Saccharomyces cerevisiae*, although other species are commercially available and can be used. Furthermore, cell cultures can be grown which are derived from mammalian cells. Some examples of suitable host cell lines include embryonal kidney (293), SW-13, chinese hamster ovary (CHO), HeLa, myeloma, Jurkat, COS-1, BHK, W138 and madin-darby canine kidney (MDCK). In the practice of the invention, the 293 cells are preferred.

UGT2B17, whether recombinantly produced as described herein, purified from nature, or otherwise produced, can be used in assays to identify compounds which inhibit or alter the activity of the enzyme. In particular, since UGT2B17 is shown to catalyze the glucuronidation process, this enzyme can be used to identify compounds which interfere with this process. It is preferred that the enzyme be obtained directly from the recombinant host, wherein following expression, a crude homogenate is prepared which includes the enzyme. A substrate of the enzyme, such as androsterone and a compound to be tested are then mixed with the homogenate. The activity of the enzyme with and without the test compound is compared. Numerous methods are known which can be used to indicate the effects of the test compound on the activity of the substrate for easy detection of the relative amounts of substrate and product over time. For example, it is possible to label the substrate so that the label also stays on any product that is formed. Radioactive labels, such as $C^{14}$ or $H^3$, which can be quantitatively analyzed are particularly useful.

It is preferred that the mixture of the enzyme, test compound and substrate be allowed to incubate for a predetermined amount of time. In addition, it is preferred that the product is separated from the substrate for easier analysis. A number of separation techniques are known, for example, thin layer chromatography (TLC), high pressure liquid chromatography (HPLC), spectrophotometry, gas chromatography, mass spectrophotometry and nuclear magnetic resonance (NMR). However, any known method which can differentiate between a substrate and a product can be used.

In addition, compositions which include the protein, or a fragment thereof or antibodies to the protein, or to antigenic fragments thereof can be produced. These compositions are contacted with samples, such as body fluids or tissues which are suspected of containing UGT2B17 antibodies or UGT2B17. After contact known methods are used to determine the extent to which antigen/antibody complexes are formed.

The preferred techniques for detecting the formation of antigen/antibody complexes include, but are not limited to, enzyme-linked immunosorbent assay (ELISA), indirect fluorescence assay, latex agglutination, radioimmunoassay (RIA), and liposome-based assay. Alternatively, a Western blot technique may be used, in which case the bands are detected by visual inspection, and substantial appearance of dark bands may be taken as a positive indication. In addition, in vivo assays may be used, wherein labelled antibodies against the antigen are used to detect the presence of UGT2B17 in vivo.

In preferred embodiments of the invention, the antigen or antibody compositions of the invention are immobilized and contacted with the sample to be tested. After washing away the sample and any antibodies or antigens which did not bind, standard methods are used to determine the extent to which the antigens and antibodies are bound.

Before contacting a test sample with antigenic or antibody compounds in accordance with the invention, it is preferred (but not necessary) that the antigenic or antibody composition be immobilized using conventional techniques (e.g. ELISA). In an embodiment, liposome-based assays may be used, as described in more detail below. For conventional immobilization, polystyrene plates, for example, may be incubated with antigenic or antibody suspensions made in accordance with the invention. Alternatively, for example, antigens isolated as protein bands on electrophoretic gel may be transferred to a nitrocellulose sheet by known methods. See Towbin et al., *Proc. Nat'l. Acad. Sci.*, 76: 4350–54 (1979); Burnette et al., *Biochem.*, 112: 195–203 (1981). Numerous other techniques are known in the art for binding antigens or antibodies to substantially inert substrates.

Bound antigens in accordance with the invention are preferably contacted with a dilute fluid which includes the sample to be tested for presence of antibody to UGT2B17. The antigen and sample are preferably incubated for at least 5 to 15 minutes. Less time is needed when incubation proceeds at or near human body temperature, about 37° C. Incubation at other temperatures, for instances 4° C., is also proper, but generally requires additional incubation time. Preferred incubation time at 37° is from about 5 minutes to about 90 minutes. The bound antigens should then be rinsed to remove any unbound antibodies, i.e., those which are not specific for the antigens. Preferably, rinsing proceeds with a buffer solution such as PBS T, PBS TT or Tris/Tween/Sodium chloride/azide. Multiple rinsings are preferred.

During incubation, UGT2B17 specific antibodies bind to the immobilized antigens to create antigen/antibody complexes. All unbound antibodies are substantially removed during the rinsing procedure. Due to the high specificity of the antigens of the invention, antibodies which are not specific for UGT2B17 are substantially removed by the rinsing. Naturally, if the tested sample did not contain UGT2B17 specific antibodies, the immobilized antigens would be substantially free of human antibody, and subsequent testing for antigen/antibody complexes should not indicate a substantial presence of such complexes. On the other hand, if the tested sample were rich in UGT2B17-specific antibodies, these antibodies should have bound to the immobilized antigens to form a large quantity of antigen/antibody complex for subsequent detection.

Detection of antigen/antibody complex may be achieved by a wide variety of known methods. Preferred methods include but are not limited to enzyme-linked immunosorbent assay, latex agglutination. Western blot technique or indirect immunofluorescence assay.

Typically, the UGT2B17-specific antibodies complexed with immobilized antigen are detected by contact with labelled or otherwise detectable second antibodies specific for the immunoglobulin being tested for (the anti-UGT2B17). If the test sample is human sera, for example, the detectable second antibody is specific for human immunoglobulin. The labelled second antibodies may be specific for any human antibody, such as IgG or IgA. When acute sero-conversion is suspected, an IgM test using a labelled second antibody specific for IgM may be appropriate. The second antibodies are preferably incubated with the immobilized antigens for about 5 minutes to about 2 hours, preferably 30 minutes to 60 minutes at a temperature of about 20° C. to about 37° C. Then, the antigens are washed with a buffer solution (preferably multiple times) in order to remove all unbound labelled antibody. The washings will remove substantially all labelled antibody except that which has bound to immunoglobulin present on the antigens. Of course, substantially the only human immunoglobulin present at his point should be UGT2B17-specific antibody. Hence, the presence of UGT2B17-specific antibody may be indirectly measured by determining the presence or absence of the labelled second antibody.

There are many known techniques for detecting the label, which vary with the type of label used. For instance, fluorescein-labelled antibody may be detected by scanning for emitted light at the characteristic wavelength for fluorescein. Alternatively, an enzyme label is detected by incubation with appropriate substrate and detection of any enzymatic activity, preferably activity resulting in a color change. Such activity can be determined by visual inspection or can be read automatically by a spectrophotometer set at the appropriate wavelength.

For example, the enzyme label may be horseradish peroxidase and the substrate may be $H_2O_2$ and 2,2'-azinobis(3-ethylbenzothiazoline-6-sulfonic acid) which produces in the presence of the enzyme, a compound detectable by a spectrophotometer set at 414 nm.

In Western blotting, the positive signal may be detected when an enzyme is conjugated to the second antibody. Incubation with appropriate substrate enzymatically produces a color product in the immediate vicinity of the antigenic band resolved by this process. The presence of a reactive band may be detected by visual inspection. In an indirect immunofluorescence assay, fluorescein-labelled second antibodies may be detected by fluorescence-activated detectors, or by visual inspection.

A liposome-based assay may involve the presence of fluorescein, an enzyme or a substrate inside a liposome onto whose surface UGT2B17 antigens are expressed. These liposomes are incubated with a diluted body fluid sample to be tested, and are thoroughly washed. Any liposomes with immunoglobulins on their surface forming an antigen/antibody complex may be recognized by attaching a second antibody, specific to the immunoglobulin being tested for, onto the inside walls of a polystyrene tube containing the liposomes. Liposomes having antibody bound to their surfaces will become immobilized on the tube walls, and non-immobilized will be washed away. The liposomes can be lysed with, for instance, detergent, or complement, and the enzyme or substrate that was in the interior is now free to react with the complementary substrate (or enzyme) in the solution in the tube. Enzymatic activity, preferably a color change reaction could be detected by visual inspection or spectrophotometric color determination.

It is also possible to use antibodies to UGT2B17 or to an antigenic portion thereof to detect antigens in a test sample. The techniques and methodology used are similar to those described above, except that antibodies are immobilized, samples suspected of containing UGT2B17 are tested and labelled anti-UGT2B17 is used to detect formation of complexes between UGT2B17 and the immobilized antibodies.

UGT2B17-specific test kits can be constructed for detecting antibodies or antigens using several different techniques for detection. A test kit for antibody or antigen detection may include a compartmented enclosure containing a plurality of wells, plates which were coated prior to use with UGT2B17 antigen or antibody, and ELISA materials for enzyme detection, and a color change indicator. Naturally, a variety of enzymes and developers can be used.

A second test kit for detecting antibodies using the Western blot technique may be comprised of a container, cover, nitrocellulose sheet, and a polyacrylamide slab gel in the presence of sodium dodecyl sulfate, surfactants, pH modifiers, dried non-fat milk and materials for enzyme detection including a color change indicator, such as DAG in Tris with hydrogen peroxide. This Western blot analysis kit also contains peroxidase-labelled goat or rabbit anti-human immunoglobulin and a source of UGT2B17 antigens.

Another UGT2B17-specific test kit for detecting antibodies or antigens using the indirect immunofluorescence assay may include a compartmental container with UGT2B17 antigens or antibodies, phosphate buffered saline and a fluorescent labelled conjugate.

Finally, a different UGT2B17-specific test kit for detecting antibodies or antigens uses liposomes and comprises a container, fluorescent marker- (or enzyme- or substrate-) filled liposome with UGT2B17 antigens or antibodies on their surface, and a surface-active agent. In this assay, the container might be a precoated tube or well with the appropriate conjugate.

The extent of detection of the antigen/antibody complex which should be considered a positive signal depends upon the detection mean chosen, but may be defined generically as a value greater than the mean plus one (1) interval of standard deviation from the results observed from a negative control group, all other parameters (e.g. dilution of sample, time of incubation) being held constant. In some embodiments, where a higher specificity is desired, mean plus two or mean plus three standard deviations may be utilized.

It is also contemplated that the gene for UGT2B17 or a portion thereof can be used to produce antisense nucleic acid sequences for inhibiting expression of UGT2B17 in vivo. Thus, the activity of the enzyme and the levels of its substrates (e.g. androgens) may be increased where desirable. In general, antisense nucleic acid sequences can interfere with transcription, splicing or translation processes. Antisense sequences can prevent transcription by forming a triple helix or hybridizing to an opened loop which is created by RNA polymerase or hybridizing to nascent RNA. On the other hand, splicing can advantageously be interfered with if the antisense sequences bind at the intersection of an exon and an intron. Finally, translation can be affected by blocking the binding of initiation factors or by preventing the assembly of ribosomal subunits at the start codon or by blocking the ribosome from the coding portion of the mRNA, preferably by using RNA that is antisense to the message. For further general information, see Hélène et al., *Biochimica et Biophysica Acta,* 1049:99–125 (1990), which is herein incorporated by reference in its entirety.

An antisense nucleic acid sequence is an RNA or single stranded DNA sequence which is complementary to the target portion of the target gene. These antisense sequences are introduced into cells where the complementary strand base pairs with the target portion of the target gene, thereby blocking the transcriptions splicing or translation of the gene and eliminating or reducing the production of UGT2B17. The length of the antisense nucleic acid sequence need be no more than is sufficient to interfere with the transcription, splicing or translation of functional UGT2B17. Antisense strands can range in size from 10 nucleotides to the complete gene, however, about 10 to 50 nucleotides are preferred, and 15 to 25 nucleotides are most preferred.

Although it is contemplated that any portion of the gene could be used to produce antisense sequences, it is preferred that the antisense is directed to the coding portion of the gene or to the sequence around the translation initiation site of the mRNA or to a portion of the promoter. It is preferred to use a portion including amino acids 1 through 295 and, most preferable to use a portion which includes amino acids 54 and 227.

As is well understood in the art, the sequences can be modified in various manners in order to increase the effectiveness of the treatment. In particular, the sequences can be modified to include additional RNA on the 3' end of the RNA which can form a hairpin-loop structure and thereby prevent degradation by nucleases. In addition, the chemical linkages in the backbone of the oligonucleotides can be modified to prevent cleavage by nucleases.

There are numerous methods which are known in the art for introducing the antisense strands into cells. One strategy is to incorporate the gene which encodes UGT2B17 in the opposite orientation in a vector so that the RNA which is transcribed from the plasmid is complementary to the mRNA transcribed from the cellular gene. A strong promoter, such as pCMV, is generally included in the vector, upstream of the gene sequence, so that a large amount of the antisense RNA is produced and is available for binding sense mRNA. The vectors are then transfected into cells which are then administered. It is also possible to produce single stranded DNA oligonucleotides or antisense RNA and incorporate these into cells or liposomes which are then administered. The use of liposomes, such as those described in WO95/03788, which is herein incorporated by reference, is preferred. However, other methods which are well understood in the art can also be used to introduce the antisense strands into cells and to administer to these patients in need of such treatment.

The following is a description of the materials and methods used in the isolation of a UGT2B17 cDNA clone. In addition the materials and methods used in the expression of UGT2B17 and the determination of substrate specificity are provided below. These examples are intended to be illustrative of the invention and it is well understood by those of skill in the art that modifications and alterations in the procedure and source and/or different techniques can be used within the scope of the invention. In addition, it is well understood that the gene can be produced using recombinant techniques.

Materials. UDP-glucuronic acid and all aglycons were obtained from Sigma Chemical Co. (St. Louis, Mo.) and ICN Pharmaceutical, Inc. (Montreal, Canada). Radioinert steroids were purchased from Steraloids Inc. (Wilton, N.H.). [9,11-$^3$H] androsterone (59 Ci/mmol), [9,11-$^3$H] androstane-3α, 17β-diol (56 Ci/mmol) and [$^{14}$C]UDP-glucuronic acid (285 mCi/mmol) were obtained from NEN Dupont (Boston, Mass.). [1,2-$^3$H] dihydrotestosterone (47 Ci/mmol), [1, 2, 6, 7-$^3$H] testosterone (90 Ci/mmol), α-[$^{32}$P]-dCTP (3000 Ci/mmol) and α-[$^{32}$P]-dUTP (3000 Ci/mmol) were obtained from Amersham (Oakville, Canada). Geneticin (G418) and Lipofectin were obtained from Gibco BRL (Burlington, Canada). Protein assay reagents were obtained from Bio-Rad (Richmond, Calif.). Restriction enzymes and other molecular biology reagents were obtained from Pharmacia LKB Biotechnology Inc. ( Milwaukee, Wis.), Gibco BRL (Burlington, Canada), Stratagene (La Jolla, Calif.) and Boehringer Mannheim (Indianapolis, Ind.). AmpliTaq DNA polymerase was from Perkin-Elmer Cetus (Branchburg, N.J.). Human embryonic kidney 293 cells (HK293) and LNCaP cells were obtained from the American Type Culture Collection (Rockville, Md.). Total RNA from human prostate, adrenal, testis, mammary gland, kidney, uterus and lung was purchased from Clontech (Palo Alto, Calif.).

Human RNA Isolation. Total RNA was isolated from human liver, adipose tissue, skin, placenta, benign prostate hyperplasia tissue (BPH) and LNCaP cells according to the Tri reagent acid phenol protocol as specified by the supplier (Molecular Research Center Inc., Cincinnati, Ohio). The mRNAs obtained from human prostate hyperplastic tissue (BPH) and LNCaP cells were affinity purified by chromatography through oligo(dT)cellulose (Pharmacia, Milwaukee, Wis.).

cDNA Isolation. Affinity purified BPH and LNCaP cell mRNAs were used to construct cDNA libraries in the ZAP Express vector as specified by the supplier (Stratagene, La Jolla, Calif.). The filters were prehybridized in 40% formamide, 5X Denhardt's solution, 5X SSPE, 0.1% SDS and 100 mg/ml salmon sperm DNA for 4 hours at 42° C. The hybridization was performed in the same solution for 16 hours at 42° C. with 2.0x10$^6$ cpm/ml of a pool of probes derived from UGT2B7, UGT2B10 and UGT2B15 cDNAs. The cDNA probes were radiolabelled by the random primer technique in the presence of [α-$^{32}$P]dCTP. The filters were washed twice in 2X SSC, 0.1% SDS at 42° C. for 15 minutes and then the filters were exposed for two days at 80° C. on XAR5 film with an intensifying screen (Kodak Corp., Rochester, N.Y.).

Approximately 1x10$^6$ recombinants were screened. Thirty positive clones were isolated from the LNCaP cell library and five positive clones were isolated from the BPH cDNA library. Of these clones, two clones from the LNCaP library and one clone from the BPH library were found to encode UGT2B17. The three cDNA clones were sequenced in both directions using specific UGT oligonucleotides and were found to be identical except for the length of their 5' untranslated region and the number of residues in the poly (A+) tail.

Stable Expression of UGT2B17. Human kidney 293 cells were grown in Dubelcco's modified Eagle's medium containing 4.5 g/l glucose, 10 mM HEPES, 110 μg/ml sodium pyruvate, 100 IU of penicillin/ml, 100 μg/ml of streptomycin and 10% fetal bovine serum (FBS) in a humidified incubator, with an atmosphere of 5% $CO_2$, at 37° C. 5 μg of pBK-CMV-UGT2B17 was used to transfect HK293 cells using Lipofectin and following the manufacturer's instructions (Gibco BRL: Burlington, Canada). Forty-eight hours after transfection, stable transfectants were selected in a media containing 800 μg/ml G418. After five rounds of selection, a clonal cell line which stably expressed a high level of UGT2B17 was isolated.

Activity of the UGT2B17 Enzyme. The UGT2B17 protein was expressed by excising the cDNA encoding the UGT2B17 enzyme into a pBK-CMV vector. The pBK-CMV-UGT2B17 construct was then transcribed in vitro using T3 polymerase and the resulting transcript was translated using a rabbit reticulocyte system. The expressed protein was found to have a molecular weight of 53 kilodaltons.

Glucuronidation Assay Using Cell Homogenates. HK293 cells expressing UGT2B17 were suspended in a Tris buffered saline containing 0.5 mM DTT and were homogenized using a Brinkman polytron. Enzyme assays were performed using [$^{14}$C] UDP-glucuronic acid (UDPGP), 500 μM of the various aglycones and 150 μg of protein from cell homogenates in 50 mM Tris-HCl (pH 7.5), 10 mM $MgCl_2$, 100 μg/ml phosphatidylcholine and 8.5 mM saccharolactone in a final volume of 100 μl. The enzyme assays were terminated by adding 100 μl of methanol, and the tubes were centrifuged at 14,000 g for 1 minute to remove the precipitated proteins. 100 μl of the aqueous phase was applied onto thin layer chromatography (TLC) plates (0.25 mm thick silica gel, 60 $F_{254}$ S) (EM Science, Gibbstown, N.J.) and then was chromatographed in a solvent of toluene:methanol:acetic acid in the proportion of 7:3:1. The TLC plates were exposed for four days and the extent of glucuronidation was measured by Phosphorimager (Molecular Dynamics).

Assays were conducted to screen for substrates which react with UGT2B17 in which the substrate was exposed to 6 μM of [$^{14}$C]UDPGA and 94 μM of unlabelled UDPGA for 16 hours at 30° C. The compounds which demonstrated reactivity to UGT2B17 in the screening assay were subsequently reassayed to determine the amount of enzyme activity. In the second assay, the substrate was exposed to 6 μM [14C] UDPGA and 494 μM of unlabelled UDPGA for 15 minutes at 30° C. The enzyme reaction is linear for 30 minutes at these conditions when the Km of UDPGA is 200 μM. No glucuronidation activity was detected in nontransfected HK293 cells.

Figure 3:
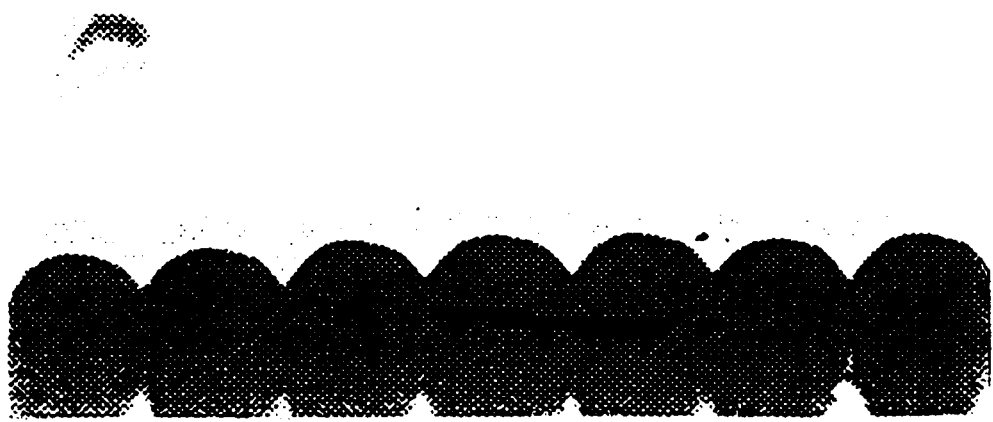
FIG. 3 provides the results of an assay to determine the specificity of UGT2B17 for androgenic compounds.

As described above, the enzymatic activity of UGT2B17 was evaluated by transfecting HK293 cells with vectors which included the gene encoding UGT2B17. As shown in FIG. 3, the HK293 cell homogenate containing the stably expressed UGT2B17 was analyzed for aglycon specificity using TLC. As shown in Table 1, over sixty endogenous and exogenous substances were tested for activity and of these, it was found that 25 compounds were glucuronidated by UGT2B17. There was no glucuronidation of the compounds in the control HK293 cell homogenates which did not contain the UGT2B17 protein.

| Compound | Initial Screening | Glucuronide Formation (pmol/min/mg protein) | Compound | Initial Screening | Glucuronide Formation |
|---|---|---|---|---|---|
| $C_{19}$ STEROIDS | | | $C_{21}$ STEROIDS | | |
| Testosterone | + | 9 | Progesterone | − | |
| Dihydrotestosterone | + | 14 | 17-OH-Progesterone | − | |
| Androsterone | + | 5 | Pregnenolone | − | |
| Epiandrosterone | − | | 17-OH-Pregnenolone | − | |
| Dehydroepiandrosterone | − | | 5α-pregnane-3α-ol-20-one | + | N.D. |
| Etiocholanolone | + | 13 | 5α-pregnane-3α,20α-diol | + | 8 |
| Androst-5-ene-3β,17β-diol | − | | 5α-pregnane-3α,17α-diol-20-one | − | |
| 5α-Androstane-3α,17β-diol | + | 15 | 5α-pregnane-3β,17α-diol-11-20-one | − | |
| 5α-Androstane-3β,17β-diol | − | | 5α-pregnane-3β,17α-diol-20-one | + | N.D. |
| 5α-Androstane-3α,11β,17β-triol | + | 8 | 5β-pregnane-3α-20α-diol | − | |
| 5α-Androstane-3α,11α,17β-triol | + | 5 | 5β-pregnane-3α,17α-diol-20-one | + | N.D. |
| 5β-Androstane-3α,17β-diol | + | 14 | 5β-pregnane-3α,6α,17α-triol-20-one | − | |
| 5β-Androstane-3α,16α,17β-triol | + | 11 | 11-Deoxycortisol | − | |
| 5β-Androstane-3α,11α,17β-triol | + | N.D. | BILE ACIDS | | |
| | | | Lithocholic acid | − | |
| $C_{18}$ STEROIDS | | | | | |
| Estrone | − | | Bilirubin | − | |
| Estradiol | − | | Chenodeoxycholic acid | − | |
| Estriol | − | | Hyodeoxycholic acid | − | |
| 1,3,5,10-Estratriene-3,16α-diol-17-one | + | N.D. | OTHER ENDOGENOUS COMPOUNDS | | |
| 1,3,5,10-Estratriene-2,3,17β-triol | + | N.D. | $T_3$ | − | |
| 1,3,5,10-Estratriene-2,3-diol-17-one | + | N.D. | $T_4$ | − | |
| 1,3,5,10-Estratriene-3,4,17β-triol | + | N.D. | Retinoic acid | − | |
| 1,3,5,10-Estratriene-2,3,16α,17β-tetrol | + | N.D. | Vitamin $D_3$ | − | |
| 1,3,5,10-Estratriene-3,4-diol-17-one | + | N.D. | Vitamin C | − | |
| NEUROMODULATORS | | | Cholesterol | − | |
| 5-hydroxytryptamine | − | | OTHER EXOGENOUS COMPOUNDS | | |
| Serotonine | − | | Imipramine | − | |
| PHENOLIC SUBSTRATES | | | OH-flutamide | − | |
| Eugenol | + | 38 | 4-methyllumbelliferone | + | N.D. |
| p-nitrophenol | + | 4 | | | |
| o,o' biphenyl | + | 7 | | | |
| p,p' biphenyl | + | 5 | | | |
| 4-aminophenol | − | | | | |
| phenolphtalein | − | | | | |
| l-naphtol | + | 7 | | | |

The following compounds, which are 3α and 17β hydroxyandrogens, were identified as the major endogenous substrates:
Dihydrotestosterone
Testosterone
Androsterone
Androstane-3α, 17β-diol
Androstane-3β, 17β-diol
Androst-5-ene-3β, 17β-diol Further, as set forth in Table 1, of the androgens tested, testosterone and its 5α-reduced metabolites, DHT, 3α-DIOL and ADT are the preferred substrates for UGT2B17 glucuronidation.

Figure 4A:
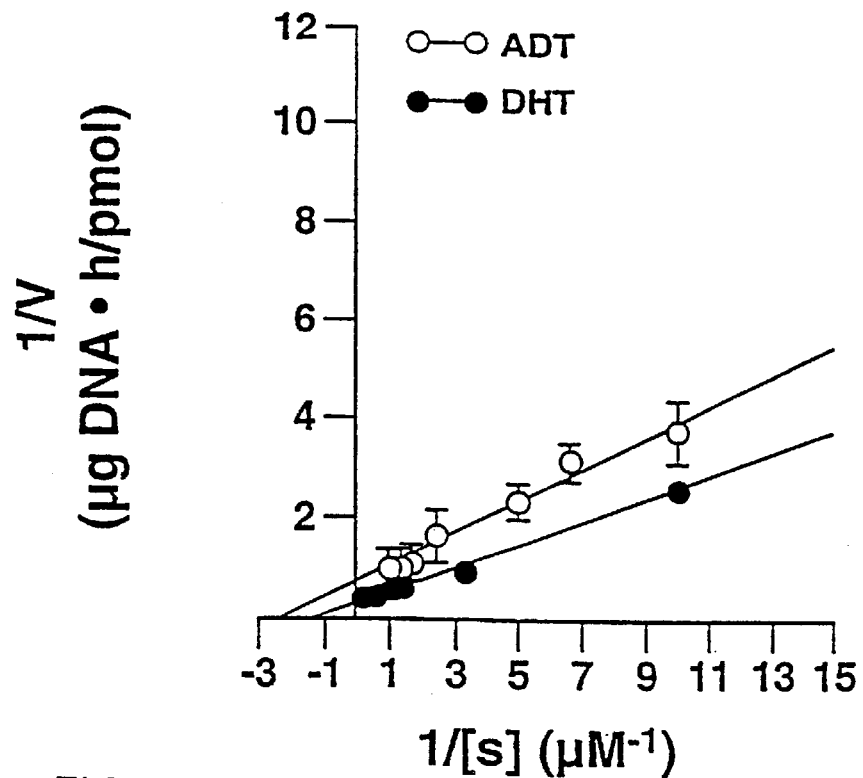
Figure 4B:
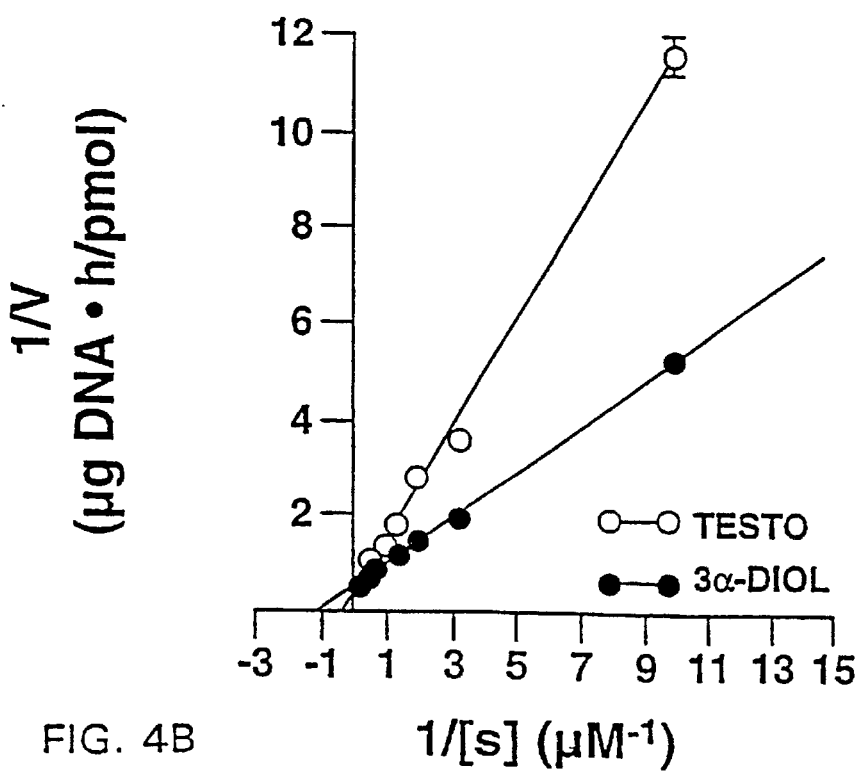

A kinetic analysis was also performed to further characterize the specificity of UGT2B17 for ADT, DHT, 3α-DIOL and testosterone. As shown in FIGS. 4A and 4B, the affinity of the enzyme for ADT, DHT, 3α-DIOL and testosterone is similar based on their Km values.

Figure 5:
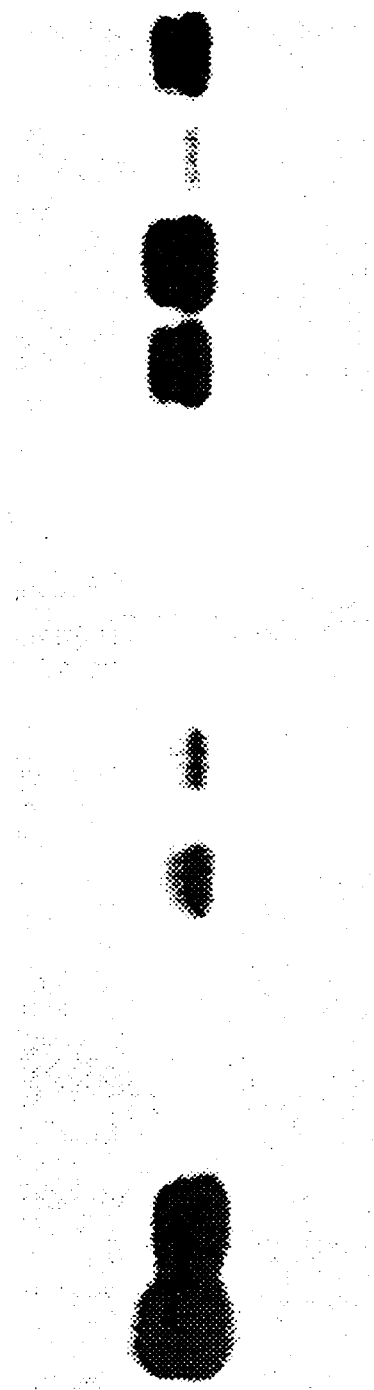
FIG. 5 provides a Southern blot indicating the presence or absence of UGT2B17 in various tissues.

FIG. 5 provides a Southern blot of a specific reverse transcriptase polymerase chain reaction (RT-PCR) analysis and shows some of the tissues in which the UGT2B17 transcript is detectable.

As such, the conversion of endogenous and exogenous compounds to glucuronide derivatives can be used to control the levels of substrates. Further, since the levels of UGT2B17 correlate with levels of androgen, a measure of the concentration of UGT2B17 can be used to indicate the levels of androgenic activity in a tissue.

Production and purification of a UGT2B17 fusion protein to make antisera. For the expression of a 29-kDa protein from amino acid sequence between 57 to 300 of UGT2B17 enzyme, HincII-SpcI fragment from UGT2B17 cDNA was subcloned into the pET23a (Novagen, Wis.) prokaryotic expression vector. The E. coli BL21 cells (Novagen, Wis.) harboring the recombinant vectors were grown at 37° C. in 1 liter of terrific broth medium supplemented with ampicillin (100 μg/ml). When the absorbance at 600 nm reached 0.5–0.6 OD U, the production of the fusion protein was achieved by adding 1 mM isopropyl β-p-thiogalactopyranoside (IPTG) fir 2 h at 37° C. The cells were harvested by centrifugation at 4° C., for 10 min at 5000×g. The bacterial pellets were resuspended in 25 ml of a lysis buffer (125 mM Tris-HCL, pH 8.0, 4.6% SDS, 10% β mercaptoethanol and 20% glycerol) and sonicated until homogeneity using an ultrasound sonicator. The proteins were separated on a preparative 12% polyacrylamide gel in the presence of SDS-PAGE and followed by two rounds of dialyses for 4 h at room temperature and 16 h at 4° C. using 50 mM Tris-HCl pH 7.5 and 50 mM Tris-HCl, pH 7.5, 150 mM NaCl.

Immunization procedure. Rabbits (Charles River Inc., Quebec, Canada) were kept in separate cages in an environmentally controlled room. They were injected at multiple sites with 500 µl of a total of 100 µg of purified fusion protein in phosphate buffered saline, in the presence of 500 µl of complete freund's adjuvant. Two booster injections were given at 6-week intervals with the same quantity of protein in the presence of incomplete Freund's adjuvant. The production of antibodies was checked 12 days after each injection on blood collected by ear puncture.

Immunoblot analysis. to gain information concerning the novel anti-UGT2B17 antibodies, microsomes from the HK293 cells, the stable HK293-UGT2B17 cells and from treated LNCaP cells were purified using a standard method, ten micrograms of each microsomal protein and one hundred nanograms of the E. coli BL21 pLys S (Novagen) strain expressing or not the fusion protein were separated on a 12% SDS-PAGE gel. The gel was transferred onto a nitrocellulose filter and probed with a dilution 1:2000 of the rabit antiserum. Antirabbit IgG horse peroxidase conjugates (Amersham, Oakville, Canada) was used as secondary antibodies, and the recognized proteins were then visualized using enhanced chemiluminescence (Renaissance, Quebec, Canada) and exposed on a hyperfilm for 1 h (Kodak Corp., Rochester, N.Y.). One hundred nanograms of E. coli BL21 (pLys S) cell lysate containing the recombinant UGT2B17 fusion protein were used to demonstrate the reactivity of the polyclonal antibody.

Reducing androgen activity with UGT2B17. LNCaP cells were transfected with UGT2B17 in the presence of a reporter construct controlled by an androgen response element so as the expression of the reporter gene is indicative of androgenic activity. The presence of the transfected UGT2B17 lead to a decreased expression of the reporter gene thereby indicating that UGT2B17 conjugates androgens and terminates the androgen response.

Although the present invention has been described in relation to particular embodiments thereof, many other variations and modifications and other uses will be apparent to those skilled in the art.

We claim:

1. An isolated nucleotide sequence encoding uridine diphospho-glucuronosyltransferase 2B17, wherein said sequence includes the coding region of nucleotide sequence SEQ ID No. 1, a nucleotide sequence encoding the same amino acid sequence as the coding region of nucleotide sequence SEQ ID No. 1, or a complement of either nucleotide sequence.

2. A recombinant expression vector comprising a promoter sequence and a nucleotide sequence in accordance with claim 1.

3. A recombinant host cell, transformed or transfected with the vector of claim 2.

4. The recombinant host cell of claim 3, wherein said host cell is a eukaryotic cell.

5. The recombinant host cell of claim 4, wherein said nucleotide sequence is integrated into the genome of said host cell.

6. The recombinant host cell, as recited in claim 4, wherein said host cell is capable of expressing a uridine diphospho-glucuronosyltransferase 2B17.

7. An isolated nucleotide sequence comprising nucleotides 52 to 927 of SEQ ID No. 1.

8. An isolated nucleotide sequence comprising nucleotides 204 to 723 of SEQ ID No. 1.

9. An isolated nucleotide sequence comprising SEQ ID No. 1.

10. An isolated nucleotide sequence encoding the amino acid sequence of SEQ ID NO. 2.

11. A method for producing uridine diphospho-glucuronosyltransferase 2B17, comprising the steps of:

preparing a recombinant host transformed or transfected with the vector of claim 2; and culturing said host under conditions which are conducive to the production of uridine diphospho-glucuronosyltransferase 2B17 by said host.

* * * * *

SEQUENCE LISTING

<160> NUMBER OF SEQ ID NOS: 2

<210> SEQ ID NO 1
<211> LENGTH: 2107
<212> TYPE: DNA
<213> ORGANISM: Homo sapiens
<220> FEATURE:
<221> NAME/KEY: CDS
<222> LOCATION: (52)..(1644)

<400> SEQUENCE: 1

```
ggcacgagga aagaaacaac aactggaaaa gaagcattgc ataagaccag g atg tct          57
                                                         Met Ser
                                                           1 ctg aaa tgg atg tca gtc ttt ctg ctg atg cag ctc agt tgt tac ttt         105
Leu Lys Trp Met Ser Val Phe Leu Leu Met Gln Leu Ser Cys Tyr Phe
          5                  10                  15 agc tct ggg agt tgt gga aag gtg ctg gtg tgg ccc aca gaa tac agc         153
Ser Ser Gly Ser Cys Gly Lys Val Leu Val Trp Pro Thr Glu Tyr Ser
     20                  25                  30 cat tgg ata aat atg aag aca atc ctg gaa gag ctt gtt cag agg ggt         201
His Trp Ile Asn Met Lys Thr Ile Leu Glu Glu Leu Val Gln Arg Gly
 35                  40                  45                  50 cat gag gtg att gtg ttg aca tct tcg gct tct att ctt gtc aat gcc         249
His Glu Val Ile Val Leu Thr Ser Ser Ala Ser Ile Leu Val Asn Ala
                 55                  60                  65 agt aaa tca tct gct att aaa tta gaa gtt tat cct aca tct tta act         297
Ser Lys Ser Ser Ala Ile Lys Leu Glu Val Tyr Pro Thr Ser Leu Thr
             70                  75                  80 aaa aat gat ttg gaa gat ttt ttt atg aaa atg ttc gat aga tgg aca         345
Lys Asn Asp Leu Glu Asp Phe Phe Met Lys Met Phe Asp Arg Trp Thr
         85                  90                  95 tat agt att tca aaa aat aca ttt tgg tca tat ttt tca caa cta caa         393
Tyr Ser Ile Ser Lys Asn Thr Phe Trp Ser Tyr Phe Ser Gln Leu Gln
    100                 105                 110 gaa ttg tgt tgg gaa tat tct gac tat aat ata aag ctc tgt gaa gat         441
Glu Leu Cys Trp Glu Tyr Ser Asp Tyr Asn Ile Lys Leu Cys Glu Asp
115                 120                 125                 130
```

-continued

```
gca gtt ttg aac aag aaa ctt atg aga aaa cta caa gag tca aaa ttt    489
Ala Val Leu Asn Lys Lys Leu Met Arg Lys Leu Gln Glu Ser Lys Phe
            135                 140                 145 gat gtc ctt ctg gca gat gcc gtt aat ccc tgt ggt gag ctg ctg gct    537
Asp Val Leu Leu Ala Asp Ala Val Asn Pro Cys Gly Glu Leu Leu Ala
        150                 155                 160 gaa cta ctt aac ata ccc ttt ctg tac agt ctc cgc ttc tct gtt ggc    585
Glu Leu Leu Asn Ile Pro Phe Leu Tyr Ser Leu Arg Phe Ser Val Gly
            165                 170                 175 tac aca gtt gag aag aat ggt gga gga ttt ctg ttc cct cct tcc tat    633
Tyr Thr Val Glu Lys Asn Gly Gly Gly Phe Leu Phe Pro Pro Ser Tyr
        180                 185                 190 gta cct gtt gtt atg tca gaa tta agt gat caa atg att ttc atg gag    681
Val Pro Val Val Met Ser Glu Leu Ser Asp Gln Met Ile Phe Met Glu
195                 200                 205                 210 agg ata aaa aat atg ata tat atg ctt tat ttt gac ttt tgg ttt caa    729
Arg Ile Lys Asn Met Ile Tyr Met Leu Tyr Phe Asp Phe Trp Phe Gln
            215                 220                 225 gca tat gat ctg aag aag tgg gac cag ttt tat agt gaa gtt cta gga    777
Ala Tyr Asp Leu Lys Lys Trp Asp Gln Phe Tyr Ser Glu Val Leu Gly
        230                 235                 240 aga ccc act aca tta ttt gag aca atg ggg aaa gct gaa atg tgg ctc    825
Arg Pro Thr Thr Leu Phe Glu Thr Met Gly Lys Ala Glu Met Trp Leu
            245                 250                 255 att cga acc tat tgg gat ttt gaa ttt cct cgc cca ttc tta cca aat    873
Ile Arg Thr Tyr Trp Asp Phe Glu Phe Pro Arg Pro Phe Leu Pro Asn
        260                 265                 270 gtt gat ttt gtt gga gga ctt cac tgt aaa cca gcc aaa ccc ttg cct    921
Val Asp Phe Val Gly Gly Leu His Cys Lys Pro Ala Lys Pro Leu Pro
275                 280                 285                 290 aag gaa atg gaa gag ttt gtg cag agc tct gga gaa aat ggt att gtg    969
Lys Glu Met Glu Glu Phe Val Gln Ser Ser Gly Glu Asn Gly Ile Val
            295                 300                 305 gtg ttt tct ctg ggg tcg atg atc agt aac atg tca gaa gaa agt gcc   1017
Val Phe Ser Leu Gly Ser Met Ile Ser Asn Met Ser Glu Glu Ser Ala
        310                 315                 320 aac atg att gca tca gcc ctt gcc cag atc cca caa aag gtt cta tgg   1065
Asn Met Ile Ala Ser Ala Leu Ala Gln Ile Pro Gln Lys Val Leu Trp
            325                 330                 335 aga ttt gat ggc aag aag cca aat act tta ggt tcc aat act cga ctg   1113
Arg Phe Asp Gly Lys Lys Pro Asn Thr Leu Gly Ser Asn Thr Arg Leu
        340                 345                 350 tat aag tgg tta ccc cag aat gac ctt ctt ggt cat ccc aaa acc aaa   1161
Tyr Lys Trp Leu Pro Gln Asn Asp Leu Leu Gly His Pro Lys Thr Lys
355                 360                 365                 370 gct ttt ata act cat ggt gga acc aat ggc atc tat gag gcg atc tac   1209
Ala Phe Ile Thr His Gly Gly Thr Asn Gly Ile Tyr Glu Ala Ile Tyr
            375                 380                 385 cat ggg atc cct atg gtg ggc att ccc ttg ttt gcg gat caa cat gat   1257
His Gly Ile Pro Met Val Gly Ile Pro Leu Phe Ala Asp Gln His Asp
        390                 395                 400 aac att gct cac atg aaa gcc aag gga gca gcc ctc agt gtg gac atc   1305
Asn Ile Ala His Met Lys Ala Lys Gly Ala Ala Leu Ser Val Asp Ile
            405                 410                 415 agg acc atg tca agt aga gat ttg ctc aat gca ttg aag tca gtc att   1353
Arg Thr Met Ser Ser Arg Asp Leu Leu Asn Ala Leu Lys Ser Val Ile
420                 425                 430 aat gac cct atc tat aaa gag aat atc atg aaa tta tca aga att cat   1401
Asn Asp Pro Ile Tyr Lys Glu Asn Ile Met Lys Leu Ser Arg Ile His
            435                 440                 445                 450
```

-continued

```
cat gat caa ccg gtg aag ccc ctg gat cga gca gtc ttc tgg att gag    1449
His Asp Gln Pro Val Lys Pro Leu Asp Arg Ala Val Phe Trp Ile Glu
            455                 460                 465 ttt gtc atg cgc cat aaa gga gcc aag cac ctt cgg gtc gca gcc cac    1497
Phe Val Met Arg His Lys Gly Ala Lys His Leu Arg Val Ala Ala His
        470                 475                 480 aac ctc acc tgg atc cag tac cac tct ttg gat gtg ata gca ttc ctg    1545
Asn Leu Thr Trp Ile Gln Tyr His Ser Leu Asp Val Ile Ala Phe Leu
    485                 490                 495 ctg gcc tgc gtg gca act atg ata ttt atg atc aca aaa tgt tgc ctg    1593
Leu Ala Cys Val Ala Thr Met Ile Phe Met Ile Thr Lys Cys Cys Leu
500                 505                 510 ttt tgt ttc cga aag ctt gcc aaa aca gga aag aag aag aaa agg gat    1641
Phe Cys Phe Arg Lys Leu Ala Lys Thr Gly Lys Lys Lys Lys Arg Asp
515                 520                 525                 530 tag ttatatcaaa agcctgaagt ggaatgacca aaagatggga ctcctccttt         1694
attccagcat ggagggtttt aaatggagga tttccttttt cctgcgacaa acgtctttt    1754 cacaacttac cctgttaagt caaaatttat tttccaggaa tttaatatgt actttagttg   1814
gaattattct atgtcaatga ttttttaagct atgaaaaata ataatataaa accttatggg  1874
cttatattga aatttattat tctaatccaa aagttacccc acacaaaagt tactgagctt   1934
ccttatgttt cacacattgt atttgaacac aaaacattaa caactccact catagtatca   1994
acattgtttt gcaaatactc agaatatttt ggcttcattt tgagcagaat ttttgtttttt  2054 aattttgcca atgaaatctt caataattaa aaaaaaaaaa aaaaaaaaaa aaa          2107
```

<210> SEQ ID NO 2
<211> LENGTH: 530
<212> TYPE: PRT
<213> ORGANISM: Homo sapiens

<400> SEQUENCE: 2

```
Met Ser Leu Lys Trp Met Ser Val Phe Leu Leu Met Gln Leu Ser Cys
 1               5                  10                  15

Tyr Phe Ser Ser Gly Ser Cys Gly Lys Val Leu Val Trp Pro Thr Glu
            20                  25                  30

Tyr Ser His Trp Ile Asn Met Lys Thr Ile Leu Glu Glu Leu Val Gln
        35                  40                  45

Arg Gly His Glu Val Ile Val Leu Thr Ser Ser Ala Ser Ile Leu Val
    50                  55                  60

Asn Ala Ser Lys Ser Ser Ala Ile Lys Leu Glu Val Tyr Pro Thr Ser
65                  70                  75                  80

Leu Thr Lys Asn Asp Leu Glu Asp Phe Phe Met Lys Met Phe Asp Arg
                85                  90                  95

Trp Thr Tyr Ser Ile Ser Lys Asn Thr Phe Trp Ser Tyr Phe Ser Gln
            100                 105                 110

Leu Gln Glu Leu Cys Trp Glu Tyr Ser Asp Tyr Asn Ile Lys Leu Cys
        115                 120                 125

Glu Asp Ala Val Leu Asn Lys Lys Leu Met Arg Lys Leu Gln Glu Ser
    130                 135                 140

Lys Phe Asp Val Leu Leu Ala Asp Ala Val Asn Pro Cys Gly Glu Leu
145                 150                 155                 160

Leu Ala Glu Leu Leu Asn Ile Pro Phe Leu Tyr Ser Leu Arg Phe Ser
                165                 170                 175
```

-continued

```
Val Gly Tyr Thr Val Glu Lys Asn Gly Gly Phe Leu Phe Pro Pro
            180                 185             190

Ser Tyr Val Pro Val Val Met Ser Glu Leu Ser Asp Gln Met Ile Phe
            195             200             205

Met Glu Arg Ile Lys Asn Met Ile Tyr Met Leu Tyr Phe Asp Phe Trp
            210             215             220

Phe Gln Ala Tyr Asp Leu Lys Lys Trp Asp Gln Phe Tyr Ser Glu Val
225                 230             235                     240

Leu Gly Arg Pro Thr Thr Leu Phe Glu Thr Met Gly Lys Ala Glu Met
                245             250                 255

Trp Leu Ile Arg Thr Tyr Trp Asp Phe Glu Phe Pro Arg Pro Phe Leu
                260             265             270

Pro Asn Val Asp Phe Val Gly Gly Leu His Cys Lys Pro Ala Lys Pro
            275             280             285

Leu Pro Lys Glu Met Glu Glu Phe Val Gln Ser Ser Gly Glu Asn Gly
            290             295             300

Ile Val Val Phe Ser Leu Gly Ser Met Ile Ser Asn Met Ser Glu Glu
305             310             315                     320

Ser Ala Asn Met Ile Ala Ser Ala Leu Ala Gln Ile Pro Gln Lys Val
                325             330                 335

Leu Trp Arg Phe Asp Gly Lys Lys Pro Asn Thr Leu Gly Ser Asn Thr
                340             345             350

Arg Leu Tyr Lys Trp Leu Pro Gln Asn Asp Leu Leu Gly His Pro Lys
            355             360             365

Thr Lys Ala Phe Ile Thr His Gly Gly Thr Asn Gly Ile Tyr Glu Ala
            370             375             380

Ile Tyr His Gly Ile Pro Met Val Gly Ile Pro Leu Phe Ala Asp Gln
385             390             395                     400

His Asp Asn Ile Ala His Met Lys Ala Lys Gly Ala Ala Leu Ser Val
                405             410             415

Asp Ile Arg Thr Met Ser Ser Arg Asp Leu Leu Asn Ala Leu Lys Ser
            420             425             430

Val Ile Asn Asp Pro Ile Tyr Lys Glu Asn Ile Met Lys Leu Ser Arg
            435             440             445

Ile His His Asp Gln Pro Val Lys Pro Leu Asp Arg Ala Val Phe Trp
            450             455             460

Ile Glu Phe Val Met Arg His Lys Gly Ala Lys His Leu Arg Val Ala
465             470             475             480

Ala His Asn Leu Thr Trp Ile Gln Tyr His Ser Leu Asp Val Ile Ala
                485             490             495

Phe Leu Leu Ala Cys Val Ala Thr Met Ile Phe Met Ile Thr Lys Cys
            500             505             510

Cys Leu Phe Cys Phe Arg Lys Leu Ala Lys Thr Gly Lys Lys Lys Lys
            515             520             525

Arg Asp
    530
```